US008660858B2

(12) United States Patent
Mullin et al.

(10) Patent No.: US 8,660,858 B2
(45) Date of Patent: Feb. 25, 2014

(54) AUTOMATED CONFIGURATION OF A MEDICAL PRACTICE MANAGEMENT SYSTEM USING GLOBAL CONTENT

(75) Inventors: Laurie Mullin, Lynnfield, MA (US); Colin Barringer, Portland, OR (US); James Chenausky, Dorchester, MA (US); Kai Chuang, Qunicy, MA (US); Christin Fetterolf, Watertown, MA (US); Richard C. Guaqueta, Cambridge, MA (US); Bradley Jordan Kriesman, Brighton, MA (US); Amit Patel, Waltham, MA (US); Adam Sterns, Watertown, MA (US); Shuang You, Cambridge, MA (US); Marjorie Otterson, Framingham, MA (US); Krista Genest, Ashland, MA (US)

(73) Assignee: athenahealth, Inc., Watertown, MA (US)

( * ) Notice: Subject to any disclaimer, the term of this patent is extended or adjusted under 35 U.S.C. 154(b) by 105 days.

(21) Appl. No.: 13/158,237

(22) Filed: Jun. 10, 2011

(65) Prior Publication Data
US 2012/0316890 A1    Dec. 13, 2012

(51) Int. Cl.
*G06Q 10/00*    (2012.01)
(52) U.S. Cl.
USPC .................................................. 705/2; 705/3

(58) Field of Classification Search
USPC ............................................................ 705/2, 4
IPC ............................................. G06Q 40/00,50/22
See application file for complete search history.

(56) References Cited

U.S. PATENT DOCUMENTS

| 5,890,129 | A | 3/1999 | Spurgeon |
| 7,343,364 | B2 | 3/2008 | Bram et al. |
| 7,720,701 | B2 | 5/2010 | Richards et al. |
| 2002/0133503 | A1 | 9/2002 | Amar et al. |
| 2008/0021732 | A1* | 1/2008 | Richards et al. .................. 705/2 |

* cited by examiner

*Primary Examiner* — John Pauls
*Assistant Examiner* — Jason Tiedeman
(74) *Attorney, Agent, or Firm* — Wolf, Greenfield & Sacks, P.C.

(57) ABSTRACT

Methods and apparatus for facilitating an automated configuration of a component of a practice management system for use by a healthcare provider associated with a medical practice. An initial configuration of the component is generated based, at least in part, on global content stored by the practice management system. A self-service implementation tool provided by the practice management system enables a user at the medical practice to refine the initial configuration via a user interface that presents the user with a plurality of tasks to perform. By allowing providers to actively participate in the configuration process by completing assigned tasks via the user interface, the process of configuring a component of the practice management system is simplified compared to conventional practice management systems, which often require an administrator of the practice management system to create a customized solution for each provider or medical practice from scratch.

24 Claims, 16 Drawing Sheets

| Table | Type | Description |
|---|---|---|
| Anatomical Drawings | Clinical content | Library of anatomical images that can be annotated using the jotter feature. |
| History of Present Illness Templates | Clinical content | HPI templates are structured according to the 1997 CMS guidelines for documenting the History of Present Illness. Each global template will include sections for Location, Duration, Quality, Severity, Onset (timing), Modifying factors, Context, and Associated Symptoms. |
| Physical Exam Templates | Clinical content | Structured clinical content that allows the provider to record information about the physical exam portion of the encounter. |
| Procedure Templates | Clinical content | Procedure templates allow providers to document commonly used procedures without manually re-entering information for each patient visit. |
| Review of Systems Templates | Clinical content | Structured clinical content that allows the provider to record information about a patient's systems during the physical exam portion of the encounter. |
| Well Child Review of Systems Templates | Clinical content | Structured clinical content that allows the provider to record information about a pediatric patient's systems during the physical exam portion of the encounter. |
| Birth History | Clinical content | Common set of problems that may have occurred during delivery of a child. |
| Family History Questions | Clinical content | Common set of questions related to a patient's family health. |
| Genetic Screening and Infection History | Clinical content | Common set of questions used during a pregnancy to assess a child's predisposition to a number of genetic diseases and infections. This information appears on the Antepartum record that will be sent to the place of delivery. |
| Gyn History | Clinical content | Common set of questions to document a patient's past gynecological history that can be used to manage future care |
| Medical History Questions | Clinical content | Common set of questions related to a patient's health history. |
| Pregnancy Problems | Clinical content | Common set of problems that may have occurred during a pregnancy. |
| Prenatal Flowsheet | Clinical content | Data elements that correspond to the Flowsheet section of the ACOG form for tracking historical encounter information during a pregnancy. |
| Prenatal History | Clinical content | Common set of problems that may have occurred during delivery of the child. |
| Social History | Clinical content | Common set of questions related to occupation, education, alcohol use, and other clinically significant information. |
| Surgical History Questions | Clinical content | Common set of questions related to the patient's surgical history. |
| Vitals | Clinical content | Common set of vital signs and units of measure. |
| Encounter and Order Group Layouts | Workflow | Encounter layouts specify the pages, sections, and ordering of sections within the encounter form. Order group layouts specify the sections used to place orders for a patient outside of the encounter. This could happen as a result of reviewing a lab/image result, a physician consult or even a patient case. |
| Clinical Paper Forms | Workflow | Commonly used templates for external communication, such as "Return to work" forms, that result from a patient encounter |
| Encounter Reasons | Workflow | Encounter Reasons describe why a patient is being seen. The Encounter Reason is selected during Intake and drives encounter layouts |
| Test Interpretation Templates | Workflow | Pre-defined structure for documenting interpretation of test results. |

Technical Requirements (.pdf)
Connectivity Testing instructions (.pdf)
Fax Forwarding Recomendations and Requirements (.pdf)
Insurance Card Scanning Technical Specifications (.pdf)

1220 → 1210 →

| Task | Due date | Completed | n/a |
|---|---|---|---|
| Order computers and printers | 12/27/2010 | ☐ | ☐ |
| Arrange for IT support (if necessary) | 12/27/2010 | ☐ | ☐ |
| Set up fax forwarding with phone company | 01/24/2011 | ☐ | ☐ |
| Configure computers and browsers for users | 01/24/2011 | ☐ | ☐ |
| Configure DYMO label printers | 01/24/2011 | ☐ | ☐ |
| Complete printer setup | 01/24/2011 | ☐ | ☐ |
| Install Dragon software for provider dictation | 01/24/2011 | ☐ | ☐ |

FIG. 12

Existing Locations add new | show deleted (8)

| | Location Name | ▲ Ordering | Default | Departments |
|---|---|---|---|---|
| edit \| delete | Fenimore Rm 1 | 40 | | • BEDFORD MEDICAL GROUP |
| edit \| delete | Fenimore Rm 2 | 50 | | • BEDFORD MEDICAL GROUP |
| edit \| delete | Lenox Rm 1 | 10 | | • 875 LENOX ROAD OFFICE |
| edit \| delete | Lenox Rm 2 | 20 | | • 875 LENOX ROAD OFFICE |
| edit \| delete | Lenox Rm 3 | 30 | | • 875 LENOX ROAD OFFICE |
| edit \| delete | Stress Room | | | |
| edit \| delete | Sub Waiting Room | | | |
| edit \| delete | Ultrasound Room | | | |
| edit \| delete | Utica Rm 1 | 80 | | • 1336 UTICA AVENUE |
| edit \| delete | Utica Rm 2 | 90 | | • 1336 UTICA AVENUE |
| edit \| delete | Utica Rm 3 | 100 | | • 1336 UTICA AVENUE |
| edit \| delete | Utica Rm 4 | 110 | | • 1336 UTICA AVENUE |
| edit \| delete | Utica Rm 8 | 150 | | • 1336 UTICA AVENUE |

FIG. 13

Encounter Reasons

Existing Encounter Reasons add new | show deleted (1)

| | Name ▲ | Provider username | Laterality | Ordering |
|---|---|---|---|---|
| edit | delete | Abdominal Pain | | | |
| edit | delete | Annual Full Physical | • skincad4 | | |
| edit | delete | Bartholin Abcess | | | |
| edit | delete | Breast Infection | | | |
| edit | delete | Breast Lump | | | |
| edit | delete | Colposcopy | | | |
| edit | delete | Contraceptive Consult | | | |
| edit | delete | Cryosurgery | | | |
| edit | delete | Depo Provera | | | |
| edit | delete | Dysmenorrhea/Painful Periods | | | |
| edit | delete | Excessive Bleeding | | | |
| edit | delete | Gyn Check | | | |
| edit | delete | Gyn Problem | • skincad4 | | |
| edit | delete | Hormone Shot | | | |
| edit | delete | HPV + Repeat Pap (Follow-up) | | | |
| edit | delete | Incision Check | | | |
| edit | delete | Infertility Consult | | | |
| edit | delete | Influenza Vaccine | • skincad4 | | |
| edit | delete | Lab only | • skincad4 | | |

FIG. 14

AUTOMATED CONFIGURATION OF A MEDICAL PRACTICE MANAGEMENT SYSTEM USING GLOBAL CONTENT

BACKGROUND

Before the advent of networked systems and computers, medical patient workflow including the entry and maintenance of patient information in medical records, was typically a manual process that involved recording patient information using paper-based forms. As the use of computers at medical practices has become more widespread, many healthcare providers have adopted procedures to enter most (or all) patient information using electronic health records (EHRs) so that the information may be readily accessible to doctors, nurses, or other clinical staff who require it. The increased accessibility of patients' medical information afforded by EHRs is just one of several factors which provide improvements over more conventional paper-based data management systems. For example, provided such data is accompanied by appropriate security measures, data stored in EHRs may be more conveniently copied to another location for backup purposes and EHRs may be more easily transferred from one hospital or clinic to another than traditional paper-based medical files. Yet another potential advantage of EHRs is the ability to store large quantities of data from a variety of sources including laboratory results, imaging results, and medical histories in a cohesive manner.

To assist with processing and managing EHRs, some medical practices may contract with a third party which provides a practice management system for managing healthcare data and facilitating patient workflows. For example, the practice management system may be a network-based system that enables medical practitioners and other medical practice staff to manage electronic health information for patients of a medical practice. The practice management system may, among other things, facilitate the management and storage of information related to patient visits, lab results, current medications, etc. to facilitate patient care at the medical practice.

SUMMARY

Although the adoption of EHRs by healthcare providers has resulted in a health information system that is more flexible than conventional paper-based systems, implementation and maintenance of an EHR data management system by many individual medical practices is often cost prohibitive. To alleviate the costs associated with maintaining a proprietary EHR data management system, as discussed above, some medical practices may contract with a third party which provides a practice management system that includes a health information management component. After a medical practice has contracted to use a practice management system, in conventional systems there is often a significant amount of time and effort required to configure the medical practice prior to allowing the medical practice to use the practice management system to enter healthcare information. Some embodiments of the invention are directed at simplifying a medical practice configuration process by enabling one or more users at a medical practice to take a more active role in the configuration process.

Some embodiments of the present invention are directed to a method of facilitating a configuration of a component of a practice management system for use by a healthcare provider associated with a medical practice. The method comprises generating, with at least one processor, an initial configuration for the component based, at least in part, on global content stored by the practice management system; receiving via a user interface, input from one or more users at the medical practice; and refining the initial configuration for the component based, at least in part, on the input received from the one or more users at the medical practice.

Some embodiments are directed to at least one computer-readable medium encoded with a plurality of instructions that, when executed by a computer, perform a method of configuring a component of a practice management system for use by a healthcare provider associated with a medical practice. The method comprises generating an initial configuration for the component based, at least in part, on global content stored by the practice management system; receiving via a user interface, input from one or more users at the medical practice; and refining the initial configuration for the component based, at least in part, on the input received from the one or more users at the medical practice.

Some embodiments are directed to a computer system comprising at least one server computer configured to host a practice management system including a health information management component, wherein the practice management system includes a configuration module configured to facilitate a configuration of the health information management component for a medical practice; and at least one client computer accessible to one or more users at the medical practice, wherein the at least one client computer is configured to display a user interface provided by the practice management system to enable the one or more users at the medical practice to participate in the configuration of the health information management component for the medical practice.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6 is listing of exemplary global content items that may be selected during pre-configuration of a customized solution in accordance with some embodiments of the invention;

FIG. 11 is a schematic of a custom wizard task to be completed by a user at a medical practice in accordance with some embodiments of the invention;

FIG. 12 is a schematic of a checklist task to be completed by a user at a medical practice in accordance with some embodiments of the invention;

FIG. 13 is a schematic of a first example of an embedded administrative task to be completed by a user at a medical practice in accordance with some of the invention;

FIG. 14 is a schematic of a first example of an embedded administrative task to be completed by a user at a medical practice in accordance with some embodiments of the invention;

DETAILED DESCRIPTION

Figure 1:
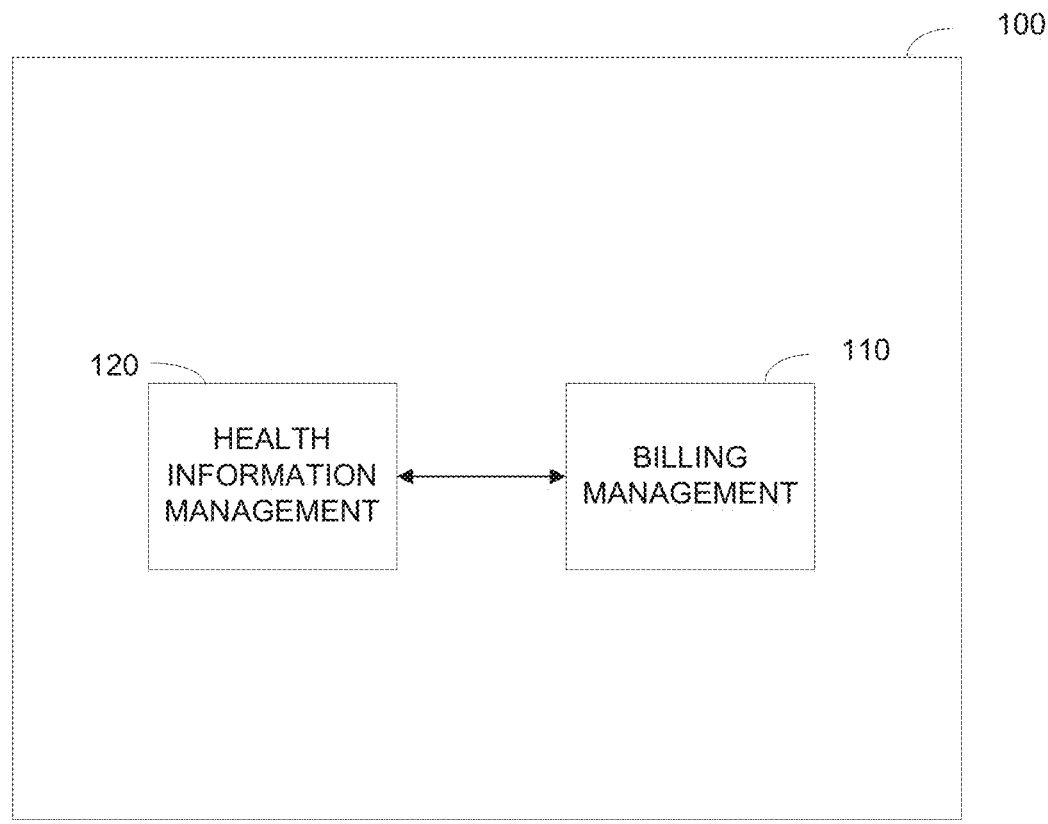
FIG. 1 is a block diagram of a practice management system in accordance with some embodiments of the invention.

The present disclosure generally relates to inventive methods and apparatus for facilitating a configuration of a medical practice to use one or more components (e.g., a healthcare information component) of a practice management system. Although particular embodiments related to configuring a health information management component of a practice management system are described in detail herein, it should be appreciated that configuration of other components of a practice management system including, but not limited to, a billing management component and a communications management component may also be configured in accordance with the methods described herein and embodiments of the invention are not limited in this respect.

As discussed above, recent widespread adoption of EHRs by medical practices has resulted in a significant need to manage large volumes of electronic health information and to improve patient workflows at medical practices to increase efficiency. To facilitate the management of healthcare information, some medical practices may contract with a third party provider of a practice management system that manages the healthcare information on behalf of providers at the medical practice.

In some conventional practice management systems, to ensure that the particular requirements of a medical practice are met, a customized and manual configuration process is employed prior to allowing the medical practice to use the practice management system for managing healthcare information. Different practices often include different medical specialties which us different types of medical forms for entering and storing healthcare information. Accordingly, for some conventional practice management systems, when a new medical practice was added, an administrator of the practice management system would typically create a customized solution for the medical practice from scratch based on the information provided by a representative of the medical practice. For example, the administrator of the practice management system may ask the representative of the medical practice a set of questions designed to elicit relevant information that the administrator needed to configure the medical practice on the practice management system. The administrator would then interpret the information provided by the representative of the medical practice to generate a customized solution.

Often, because the information provided by representative of the medical practice is incomplete, the administrator may have to ask the representative of the medical practice additional follow-up questions to acquire the information needed to generate the customized solution. Furthermore, even after the administrator has received the necessary information, when generating the customized solution different administrators may interpret the same information in different ways with the result sometimes not meeting the requirements of the medical practice. In these cases, additional reconfiguration of the healthcare information management solution may be necessary prior to use of the customized solution by the medical practice. Accordingly, due in part to the variability between administrators of a practice management system and/or variable information provided by representatives of medical practices, creation and implementation of customized solutions for a portion of a conventional practice management system may lead to inconsistent results.

The inventors have recognized and appreciated that the process of configuring a customized solution for a medical practice in a practice management system may be improved by creating an initial customized solution using stored global content commonly requested by medical practices and then allowing one or more representatives at a medical practice to interact with a self-service implementation tool to further customize the initial customized solution. To this end, some embodiments are directed to facilitating the creation of a customized healthcare information management solution within a practice management system.

In accordance with some embodiments, a practice management system, which hosts an electronic health records (EHR) system for a healthcare provider may store and manage healthcare information for a medical practice as described above. A block diagram of an exemplary practice management system that may be used to implement some embodiments of the invention is shown in FIG. 1. Practice management system 100 may be a networked system that includes a plurality of components configured to perform tasks related to specific functions within the practice management system to facilitate management of information for healthcare providers.

Exemplary practice management system 100 includes billing management component 110, which is configured to facilitate the collection and tracking of claims filed by the healthcare provider to a plurality of payers (including patients) to ensure that the healthcare provider is properly compensated for medical services rendered to patients treated by the healthcare provider. Practice management system 100 also includes health information management component 120, which is configured to store electronic health information such as EHR data for patients of the healthcare provider.

Although practice management system 100 is only shown as having two components, it should be appreciated that practice management system 100 may include any number of components that interact in any suitable way and embodiments of the invention are not limited in this respect. For example, in some embodiments, practice management system 100 may include a communications component configured to send and/or receive one or more communications with a plurality of patients having healthcare information stored by health information management component 120. Furthermore, some or all of the components in practice management system 100 may interact by sharing data, triggering actions to be performed by other components, prevent actions from being performed by other components, storing data on behalf of other components, and/or interacting in any other suitable way.

In some embodiments, practice management system 100 includes one or more storage devices configured to store configuration information for health information management component 120 and/or billing management component 110. For example, in some implementations, practice management system 100 may include one or more storage devices configured to store at least one database used to manage healthcare information associated with health information management component 120. Each medical practice subscribed to use the practice management system 100 may be associated with a local tablespace stored by the practice management system, wherein each local tablespace specifies database storage locations for information used by health information management component 120 when a user at a particular medical practice accesses practice management system 100.

Figure 2:
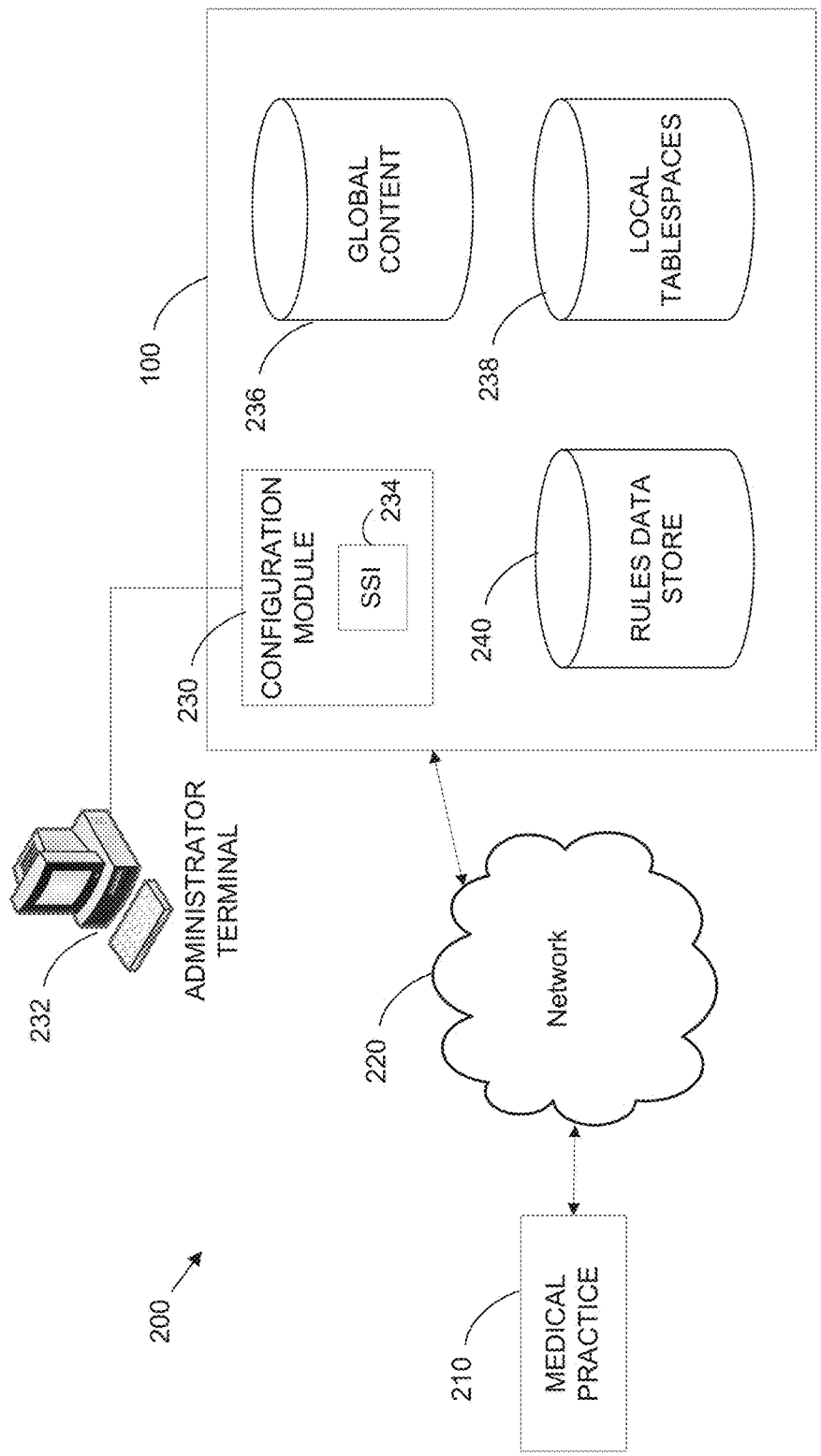
FIG. 2 is a block diagram of a computer system on which some embodiments of the invention may be employed.

FIG. 2 illustrates an exemplary networked computer system 200 on which some embodiments of the invention may be implemented. The computer system 200 includes practice management system 100 that may be connected to one or more computers at medical practice 210 via network 220. As described in further detail below, network 220 may include one or more networks for transmitting information between medical practice 210 and practice management system 100. For example, network 220 may include one or more of a public network such as the Internet and a local network such as a local area network (LAN) and embodiments of the invention are not limited by the particular network or networks that connect computer(s) at the medical practice 210 and the practice management system 100. In one implementation, the practice management system 100 hosts a web-based practice management service that enables users at the medical practice 210 to interact with a user interface to facilitate the management of healthcare data at the medical practice.

Exemplary practice management system 100 includes configuration module 230 that facilitates a configuration of one or more portions of practice management system 100 for a particular medical practice 210. In some embodiments configuration module 230 may be accessible to an administrator of the practice management system via administrator terminal 232. The administrator may interact with a user interface displayed on administrator terminal 232 to create an initial customized solution for a medical practice as discussed in more detail below.

Configuration module 230 may also include a self-service implementation tool 234 that enables one or more users at medical practice 210 to participate in a configuration process. For example, as described in more detail below, self-service implementation tool 234 may create a set of tasks for a user at the medical practice to complete to facilitate the configuration process. Self-service implementation tool 234 may also keep track of the tasks that a user has completed and provide a user with more tasks as necessary to complete the configuration process.

As described above in connection with the practice management system 100 illustrated in FIG. 1, practice management system 100 may include one or more data stores configured to store information to facilitate a configuration of portion of the practice management system 100 for use by a particular medical practice 210. For example, practice management system 100 may include global content data store 236 that is configured to store global content likely to be frequently used when configuring a customized solution for a medical practice. Global content stored by global content data store 236 may include any suitable global content including, but not limited to, templates for clinical content such as health information forms and patient workflow content such as a list of common encounter reasons.

In some embodiments, practice management system 100 may manage configurations of a portion of the practice management system 100 using one or more local tablespaces stored by local tablespaces data store 238. For example, local tablespaces data store 238 may include information mapping a configuration for a particular medical practice to information stored by practice management system 100. Local tablespaces stored by local tablespaces data store 238 and used to configure a customized solution for a medical practice in accordance with some embodiments of the invention are described in more detail below.

Practice management system 100 may also include rules data store 240 configured to store a plurality of rules that the practice management system 100 uses to manage interactions with and among one or more components of the practice management system 100. For example, rules data store 240 may include rules that send an alert to an administrator of a practice management system when a user at a medical practice has completed all of the assigned tasks in a task list. Rules data store 240 may store any suitable rules for managing portions of a practice management system and embodiments of the invention are not limited in this respect. Although only three data stores have been described with reference to practice management system 100, it should be appreciated that practice management system 100 may include any number or type of data stores and embodiments of the invention are not limited in this respect.

Some embodiments are directed to configuring a portion of a practice management system (e.g., a customized healthcare information management solution or a customized billing management solution) in which an administrator of a practice management system creates an initial customized solution using information provided by a medical practice then refines the initial customized solution using additional input from the medical practice that is received by the practice management system via an interactive user interface.

Figure 3:
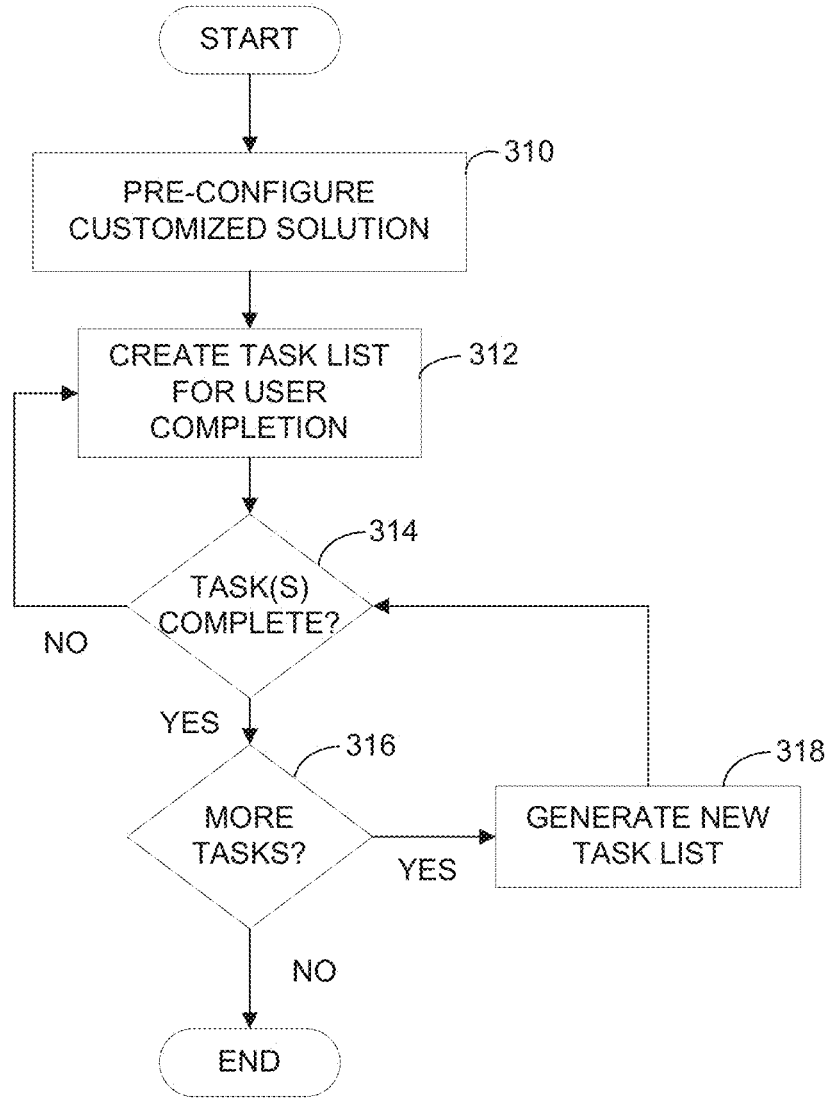
FIG. 3 is a flow chart of a configuration process for creating a customized solution for a medical practice in accordance with some embodiments of the invention.

FIG. 3 illustrates an exemplary process for configuring a customized healthcare information management solution in accordance with some embodiments of the invention. In act 310, an administrator of a practice management system (or other authorized individual) may create an initial solution for the medical practice and the initial solution may be "preconfigured" in accordance with information provided by the medical practice. In the example described above, a health information management component of a practice management system may be configured to store a local tablespace for each medical practice, wherein the data in the local tablespace describes the customized solution for the medical practice. It should be appreciated, however, that customized solutions for healthcare information management may be stored by the practice management solution in any suitable manner and using a local tablespace to describe a customized solution for a particular medical practice is discussed herein merely as an example of a particular implementation and embodiments of the invention are not limited in this respect.

After the customized solution is pre-configured, the process proceeds to act 312 where a task list is created, wherein the task list includes at least one task that one or more users at a medical practice are instructed to complete to refine the customized solution. The task list may include any suitable type of task designed to facilitate the configuration process and embodiments of the invention are not limited in this respect. For example, the task list may include, but is not limited to, tasks that prompt the user to complete a checklist, a custom wizard, or an embedded administrative item, as discussed in more detail below. The task list created in act 312 may be displayed as a portion of a user interface with which one or more users at a medical practice may interact to complete the assigned tasks in the task list to facilitate a configuration of the customized solution.

In some embodiments, the task list may be associated with a particular amount of time given by the administrator of the practice management system to complete the tasks on the list (e.g., one week) and the administrator may follow-up with the medical practice after the predetermined amount of time has elapsed to determine progress in completing the assigned tasks. Any suitable time period may be associated with the task list and embodiments of the invention are not limited in this respect. In some embodiments, the administrator of the practice management system may periodically follow-up with the medical practice regarding task completion without a particular amount of time being associated with the task list.

After creation of the task list, the process then proceeds to act 314 where it is determined whether one or more of the tasks on the task list have been completed by a user at the medical practice. The determination of whether the task(s) have been completed may be made manually by an administrator of the practice management system, automatically by a component of the practice management system, or in any other suitable way. In some embodiments, an administrator of the practice management system may periodically communicate with a user at the medical practice to discuss completion of the assigned tasks in the task list and to answer questions that may have arisen prior to the last update of the of task list.

If it is determined in act 314 that the user at the medical practice has not completed one or more tasks on the task list, the process returns to act 312 where an updated task list comprising the remaining tasks to be completed is created and presented to the user. The updated task list may be created in any suitable way. For example, items on the task list that are completed may be removed from the task list or a status associated with the completed items may be updated to reflect a completed (or partially completed) status.

If it is determined in act 314 that the user has completed the task(s) in the task list, the process proceeds to act 316 where it is determined whether there are any additional tasks for the medical practice to complete to facilitate the configuration of the customized solution. If it is determined in act 316 that there are more tasks for the medical practice to complete, the process proceeds to act 318 where a new task list comprising one or more additional tasks is generated and presented to user(s) at the medical practice for completion. After the new task list is generated in act 318, the process returns to act 314 where it is determined whether the task(s) on the new task list have been completed. The process continues until it is determined in act 316 that there are no additional tasks for the medical practice to complete at which point the process ends.

As discussed above, in some embodiments, the practice management system may include a self-service implementation tool that facilitates the creation and management of task lists within the practice management system. For example, the self-service implementation tool may separate a complete list of tasks into a particular number of stages (also called "chapters" herein) that can be managed more efficiently by a medical practice. Each stage may include tasks on a task list that are presented via a user interface to users at a medical practice at periodic intervals (e.g., one stage per week). Additionally or alternatively, task lists including tasks for different stages may be presented to users at a medical practice in a response to a request from a user at the medical practice to provide additional tasks for completion. It should be appreciated from the foregoing that tasks may be presented to a user in any suitable combination and at any suitable frequency and embodiments of the invention are not limited in the particular manner in which tasks are presented to users at a medical practice.

Figure 4:
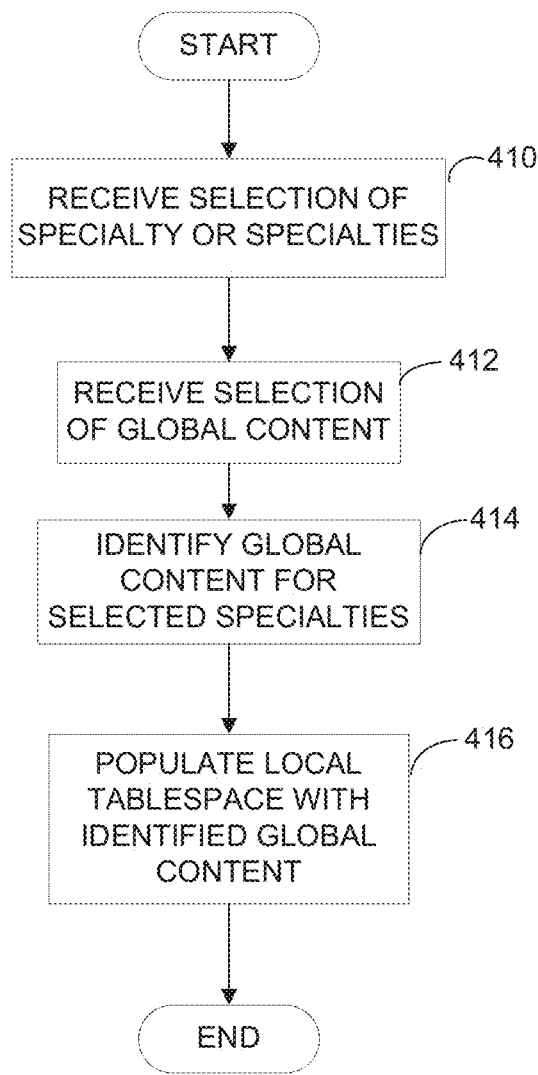
FIG. 4 is a flow chart of a pre-configuration process for creating an initial customized solution in accordance with some embodiments of the invention.

As discussed above, a first step in a configuration process may be to create an initial solution which is pre-configured using global content stored by the practice management system. FIG. 4 illustrates an exemplary pre-configuration process for a medical practice in accordance with some embodiments of the invention. In act 410, a selection of specialty or specialties associated with the medical practice is received. The information may be received in any suitable manner and embodiments of the invention are not limited in this respect. For example, when a medical practice wants to begin using a portion of a practice management system (e.g., a healthcare information component), the medical practice may sign a contract with a provider of the practice management system specifying the details of the particular configuration that the medical practice may require. An administrator of the practice management system may interact with a user interface to pre-configure an initial customized solution for the medical practice based, at least in part, on the information in the contract.

The process then proceeds to act 412 where a selection of global content associated with the desired configuration for the medical practice is received. The selection of global content may be received in any suitable manner including, but not limited to, receiving a selection of global content based, at least in part, on information in a contract between a medical practice and a provider of the practice management system.

Figure 5:
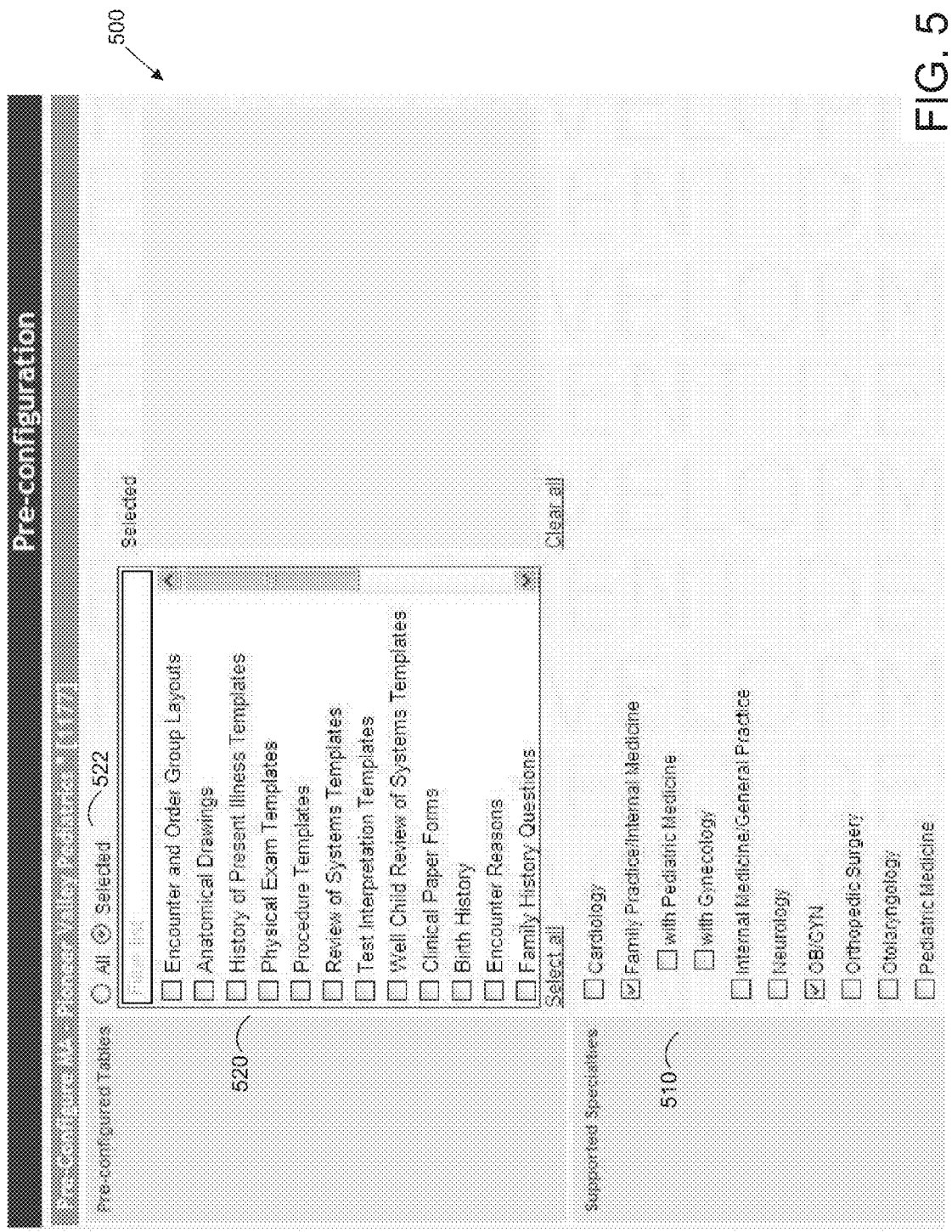
FIG. 5 is a schematic of a pre-configuration portion of a user interface for selecting specialty and global content information in accordance with some embodiments of the invention.

An exemplary pre-configuration portion 500 of a user interface with which an administrator of a practice management system may interact to pre-configure a customized solution for a medical practice in accordance with some embodiments of the invention is illustrated in FIG. 5. As shown in FIG. 5, pre-configuration portion 500 may include specialty selection section 510 and global content selection section 520 with which an administrator may interact to select one or more specialties and one or more global content items, respectively, to create an initial customized solution for a medical practice. In the example shown in FIG. 5, the specialties "Family Practice/Internal Medicine" and "OB/GYN" have been selected as the specialties provided by the medical practice. Although illustrated as a series of checkboxes, it should be appreciated that specialty selection section 510 may be implemented using any suitable selectors that enable an administrator of the practice management system to select one or more specialties.

Global content selection section 520 includes a plurality of types of global content that may be used to pre-configure a customized solution for a medical practice. As discussed above, global content may include, but is not limited to, clinical content such as procedural templates that a physician may use during an exam and patient workflow content such as a selection form for common encounter reasons for patients. Global content selection section 520 may also include an option selector 522 to enable an administrator of the practice management system to select all of the global content items displayed in global content selection section 520 or alternatively only selected global content items. The inventors have recognized that for some medical practices, it may be desirable to create an initial customized solution with as much global content as possible, particularly in a situation where the medical practice has not previously been configured to use other components of the practice management system. However, in other situations, it may be more appropriate to generate an initial solution with limited global content, perhaps based on information included in a contract between the medical practice and the provider of the practice management system or information stored in other components of the practice management system to which a healthcare provider at a medical practice is already subscribed.

Global content items displayed in global content selection section 520 may be associated with one or more specialties illustrated in specialty selection section 510 and specialties displayed in specialty selection section 520 may be associated with global content from one or more of the global content items displayed in the global content selection section 520. Associations between global content items and specialties may be stored by one or more components of the practice management system in any suitable way and embodiments of the invention are not limited in this respect.

Although specialty selection section 510 only illustrates certain specialties including Cardiology, Family Practice/Internal Medicine, Internal Medicine/General Practice, Neurology, OB/GYN, Orthopedic Surgery, Otolaryngology, and Pediatric Medicine, it should be appreciated that any suitable specialties may be included in specialty selection section 510 and the listed specialties are provided for exemplary purposes only. Additionally, although global content selection section 520 only illustrates certain global content items, any suitable global content items may be included in global content selection section 520 and embodiments of the invention are not limited in this respect. FIG. 6 illustrates some exemplary global content items that may be used in accordance with some embodiments of the invention, although it should be appreciated that any suitable number or type of global content items may be used and the global content items illustrated in FIG. 6 are provided as examples only.

Figure 7:
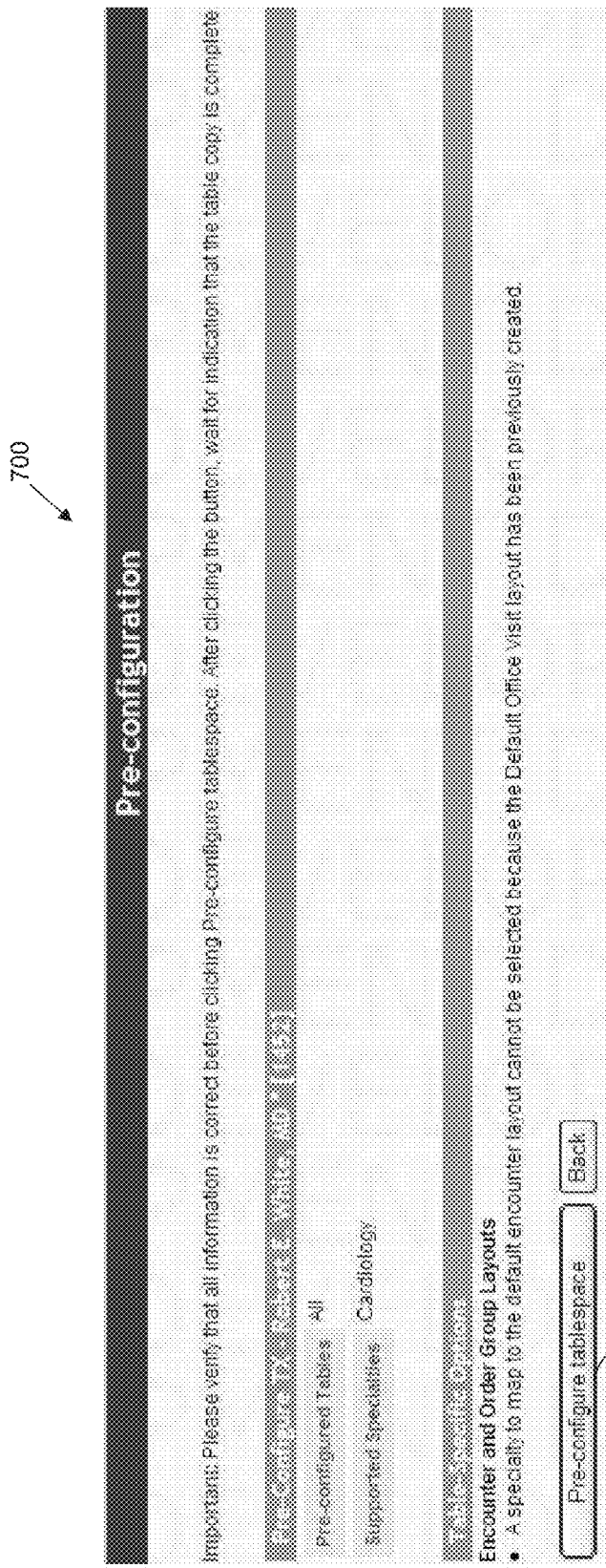
FIG. 7 is a schematic of a portion of a user interface for verifying selections in a pre-configuration process in accordance with some embodiments of the invention.

After selecting the specialty information and global content information using pre-configuration portion 500, the practice management system may be configured to display verification screen 700 as a portion of the user interface for pre-configuration as illustrated in FIG. 7. An administrator of the practice management system may view information displayed on verification screen 700 to determine that the selected specialty information and global content information is correct before proceeding with the pre-configuration process. Once the information displayed on verification screen 700 has been verified, the administrator may interact with pre-configure selector 710 to initiate the process of identifying global content associated with the selected specialty and global content selections.

Returning to the pre-configuration process illustrated in FIG. 4, after the specialty information and global content information have been selected, the process proceeds to act 414 where global content stored by the practice management system is identified based, at least in part, on the selected specialty information and global content information. As described above, the practice management system may be configured to store associations between global content items and specialties and these associations may be accessed in response to initiating a pre-configuration-process. For example, in response to the administrator interacting with pre-configure selector 710 illustrated in FIG. 7, a configuration module of the practice management system may access the stored associations to identify global content to be included in the customized solution for the medical practice.

Global content may be identified in any suitable way and embodiments of the invention are not limited in this respect. For example, in some embodiments, the practice management system may include a global content data store comprising one or more global content tables that include a plurality of entries for global content items. Global content items in the global content table(s) may be associated with one or more identifiers (e.g., "tags") that specify associations between a global content item and a specialty. Alternatively, the associations between global content items and specialties may be stored separately by the practice management system and embodiments of the invention are not limited by the particular manner in which the associations are stored and/or accessed.

After global content has been identified, the process illustrated in FIG. 4 proceeds to act 416 where the customized solution for the medical practice is populated with the information associated with the identified global content. As described above, in some embodiments, the customized solution for a medical practice may be associated with a local tablespace that includes entries for storing global content information associated with the customized solution for the medical practice. Accordingly, populating the customized solution may comprise populating the local tablespace for the medical practice with one or more entries for the global content items that were identified in act 414.

Figure 8:
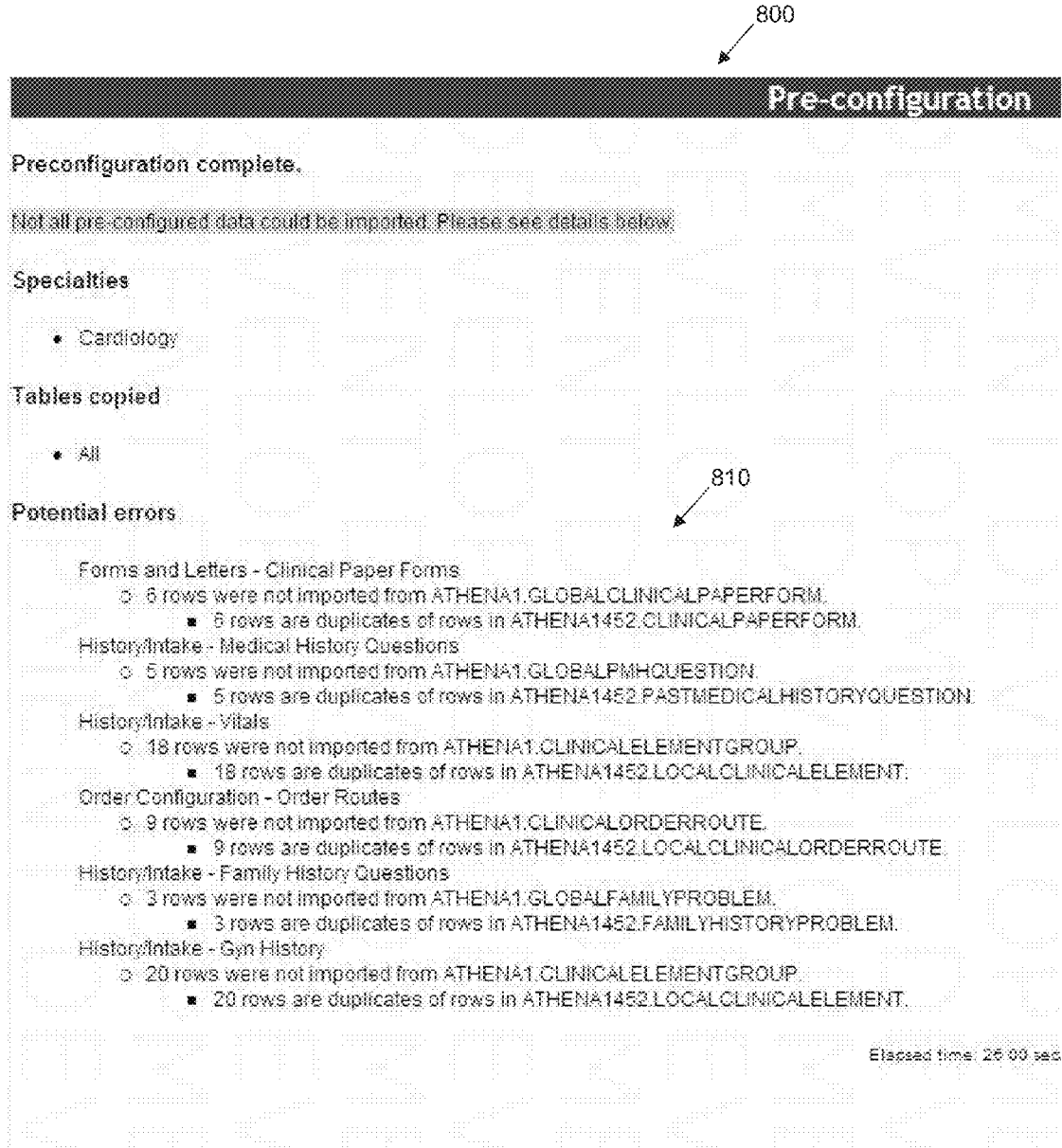
FIG. 8 is a schematic of a portion of a user interface displaying a summary of a pre-configuration process in accordance with some embodiments of the invention.

After the local tablespace has been populated with the appropriate global content in act 416, the practice management system may be configured to display as a portion of the user interface, a pre-configuration summary screen displaying the results of the pre-configuration process. An exemplary summary screen 800 is illustrated in FIG. 8. In addition to indicating that the pre-configuration process was completed, summary screen 800 may also include potential error section 810 configured to display one or more duplicate global content entries that were identified during the pre-configuration process and accordingly, were not copied multiple times to the local tablespace for the medical practice. Duplicate global content entries may be identified in any suitable manner and aspects of the invention are not limited in this way.

Figure 9:
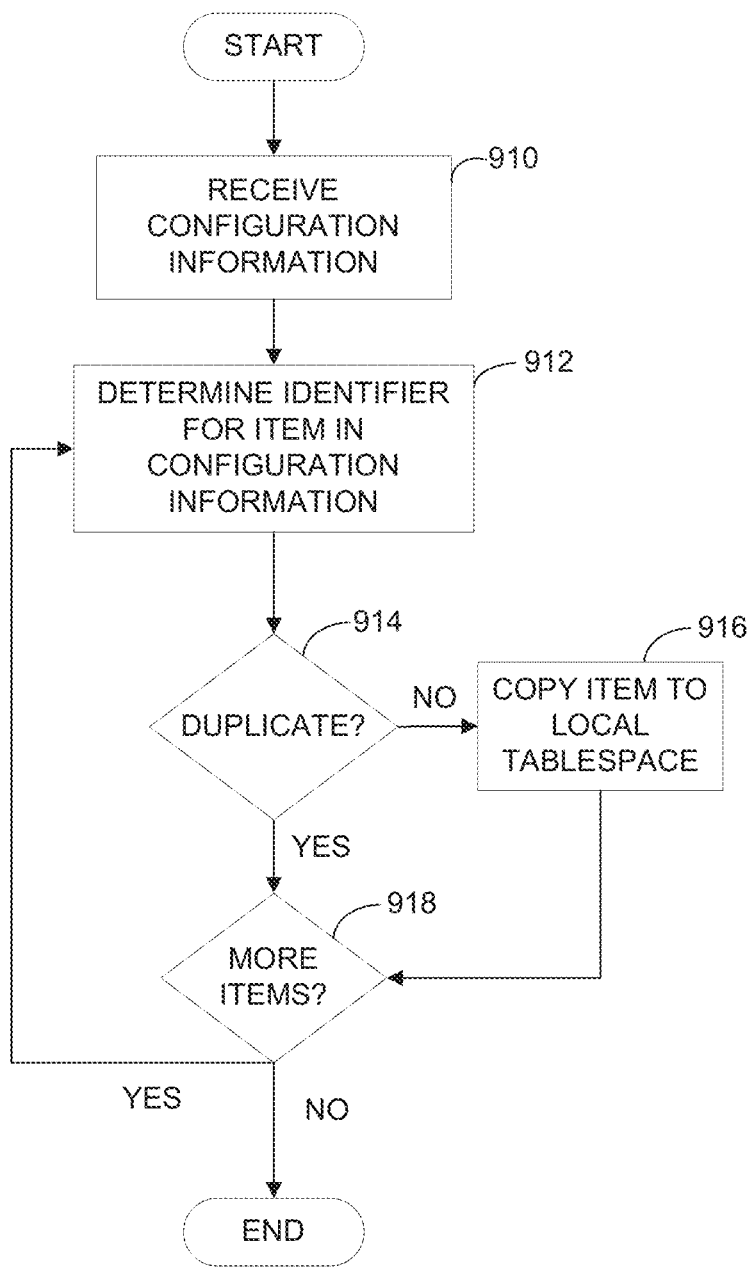
FIG. 9 is a flow chart of a pre-configuration process for identifying duplicate entries in a local tablespace in accordance with some embodiments of the invention.

FIG. 9 illustrates an exemplary process for identifying duplicate global content entries during population of a local tablespace in accordance with some embodiments of the invention. In act 910, configuration information is received. For example, the configuration information may include the identified global content items discussed above in connection with act 414 of FIG. 4. The process then proceeds to act 912 where an identifier for one or more items in the configuration information is determined. As described above, in some embodiments, information about global content items may be stored in a global content data store as entries in one or more global content tables. The entries in the global content table(s) may include one or more identifiers (e.g., tags). Among these identifiers may be a unique identifier that identifies each entry in the global content table.

Once an identifier for the global content entry in a global content table has been determined, the process proceeds to act 914 where it is determined whether the entry is a duplicate of an entry in the local tablespace. This determination may be performed in any suitable way. For example, in some embodiments, the unique identifier for the entry in a global content table may be compared with other unique identifiers in other entries in the local tablespace to determine whether the entry already exists in the local tablespace.

If it is determined in act 914 that the entry is not a duplicate, the process proceeds to act 916 where the entry is copied to the local tablespace for the medical practice. However, if it is determined in act 914 that the entry is a duplicate, the entry is not copied to the local tablespace and the fact that the entry was not copied may be reflected in potential error section 810 of summary screen 800 as illustrated in FIG. 8. Alternatively, an indication of duplicate entries may be stored, but not reported by the practice management system and embodiments of the invention are not limited in this respect.

Whether it is determined in act 914 that the entry is a duplicate or after the item is copied in act 916 to the local tablespace, the process proceeds to act 918 where it is determined whether there are additional items to be copied to the local tablespace. If it is determined in act 918 that there are additional items, the process returns to act 912 where an identifier for an additional item is determined. The process repeats until it is determined in act 918 that there are no additional items to be copied, at which point the pre-configuration process ends and, in accordance with some embodiments, the summary screen 800 is displayed to an administrator of the practice management system as described above.

As discussed earlier with respect to FIG. 2, in accordance with some embodiments, pre-configuration of a customized solution for a medical practice may result in a local tablespace for the medical practice that is populated with global content stored by the practice management system. One or more users at the medical practice may then be asked to complete one or more tasks to refine the initial configuration represented in the local tablespace. In some embodiments, this process may be facilitated by a self-service implementation tool employed by the practice management system. The tasks for the user(s) to complete may be displayed as one or more portions of a user interface that user(s) at the medical practice may interact with to complete the assigned tasks.

Figure 10:
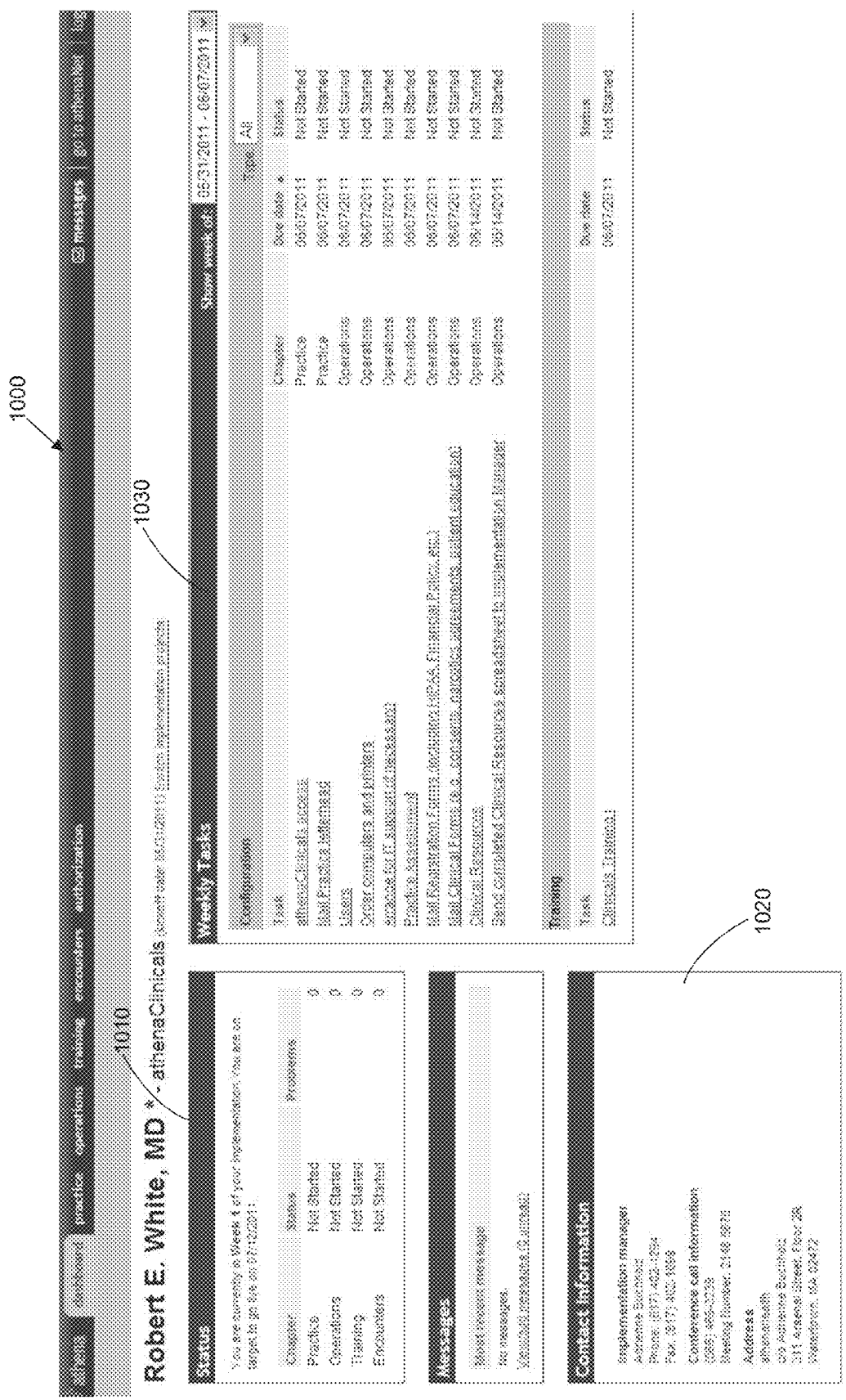
FIG. 10 is a schematic of a portion of a user interface displaying a dashboard with which a user at a medical practice may interact during a configuration process in accordance with some embodiments of the invention.

An exemplary dashboard screen 1000 that may be displayed as a portion of a user interface to a user at a medical practice once pre-configuration has been completed is illustrated in FIG. 10. Dashboard screen 1000 includes a plurality of sections that summarize information related to the implementation progress of the healthcare provider at the medical practice. For example, dashboard screen 1000 includes status section 1010, which indicates an overview of the implementation progress including a targeted "go-live" date representing the date on which the healthcare provider can begin using the practice management system for collecting data. Status section 1010 may also display an overview of the task completion for different stages or "chapters" during the self-service implementation portion of the configuration process. The information in status section 1010 may include any suitable status information and embodiments of the invention are not limited in this respect.

Dashboard screen 1000 may also include a contact section 1020, which includes contact information for an administrator of the practice management system with whom a user at the medical practice may communicate with during the self-service implementation process. Dashboard screen 1000 may also include one or more other components or sections for communicating with an administrator of the practice management system and embodiments of the invention are not limited in this respect. For example, in some embodiments, dashboard screen 1000 may include a section with which a user at the medical practice may interact to establish a live interactive chat with an administrator of the practice management system to resolve questions that may arise during the self-service implementation process.

As described earlier, during the self-service implementation portion of a configuration process in accordance with some embodiments of the invention, the practice management system provides the user(s) at the medical practice with one or more lists of tasks to complete. Accordingly, dashboard screen 1000 includes task section 1030, with which a user at the medical practice may interact to complete one or more tasks displayed in a task list. As illustrated in FIG. 10, task section 1030 may include tasks that relate to configuration of the customized solution. Task(s) related to training may additionally be included in task section 1030. The training task(s) may be configured to teach the user how to use the configured component of the practice management system and may or may not be tailored to a configuration for a particular healthcare provider or medical practice.

The configuration tasks described herein generally fall into one of three categories, although other categories of configuration tasks may alternatively or additionally be used and embodiments of the invention are not limited in this respect. Examples of each of the three categories of configuration tasks are discussed in further detail below.

A first category of configuration task is a custom wizard. Configuration tasks that invoke a custom wizard lead the user through a sequence of screens as portions of a user interface. To complete the assigned task, the user may interact with each screen in the custom wizard to provide information that is used to refine the data stored in the local tablespace for the medical practice.

Figure 11:
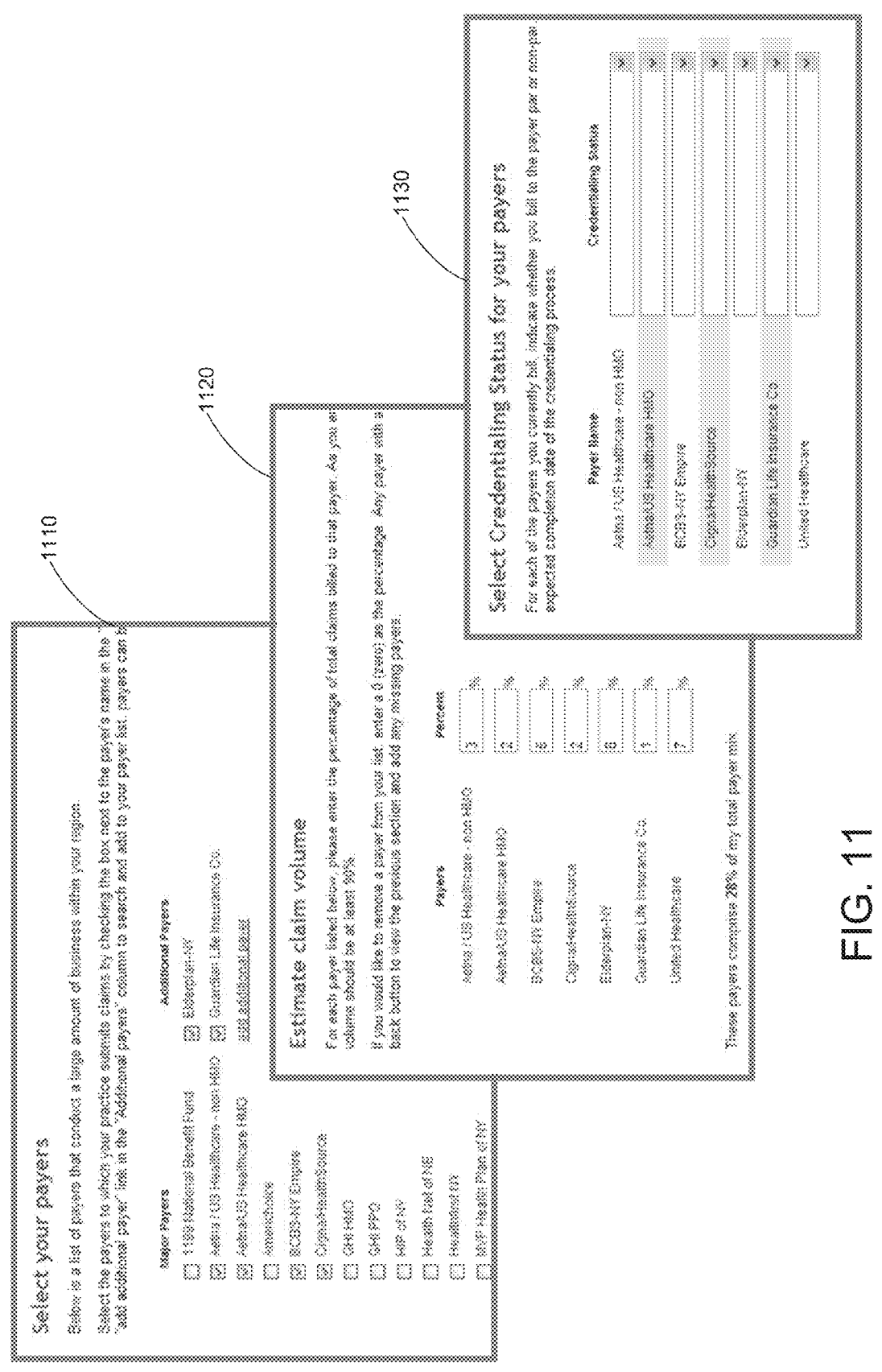

FIG. 11 illustrates an exemplary sequence of frames for a configuration task that invokes a custom wizard. The exemplary custom wizard task shown in FIG. 11 relates to inputting payer information for the healthcare provider. A first screen 1110 in the sequence of screens asks the user to select one or more payers for the healthcare provider. The user may interact with the first screen 1110 to select appropriate payers and/or to add additional payers that are not displayed in the list of payers. In some embodiments, the content in a custom wizard such as the list of payers displayed on first screen 1110 may have been generated based, at least in part, on global content stored by the practice management system as described earlier. Upon completing the first screen 1110, a second screen 1120 may displayed, which prompts the user to enter information about the amount of claims that the healthcare provider expects to send to each of the payers identified on the first screen 1110. Once the user has entered appropriate data into the second screen 1120, the custom wizard displays a third screen 1130, which relates to a credentialing status for the selected payers. The user may interact with the third screen 1130 to enter appropriate data to complete the task.

Once the task is completed, the status for the task identified on the dashboard screen may be updated to indicate that the task has been completed. The data entered using the custom wizard may be used to update the local tablespace for the medical practice stored by the practice management system. Although the exemplary custom wizard shown in FIG. 11 relates to billing procedures for a healthcare provider, it should be appreciated that a custom wizard may be designed for any suitable configuration task in which entering data on a plurality of sequential screens would be helpful.

A second category of configuration task is a checklist. The inventors have recognized that certain tasks relate to one or more actions that should be performed by a user of the medical practice but do not require the entry of data used to configure values in the local tablespace of the practice management system. To capture the performance of such tasks, some embodiments of the invention include checklist tasks, which are completed by the user by indicating whether or not the particular items on the checklist have been completed or are not applicable to the particular implementation for the medical practice.

FIG. 12 illustrates an exemplary checklist task in accordance with some embodiments of the invention. The exemplary checklist task illustrated in FIG. 12 relates to a series of actions that should be performed by a user of the medical practice to ensure that suitable connectivity between the medical practice and the practice management system may be established and maintained prior to the go-live date. In addition to including selectors 1210 for indicating when an item on the checklist has been completed, a checklist task may include due dates 1220 for completing the items on the checklist. Additionally, some checklist tasks may include links 1230 to one or more instruction documents to facilitate the completion of one or more of the items in the checklist. Although the exemplary checklist task shown in FIG. 12 relates to connectivity procedures for a healthcare provider, it should be appreciated that a checklist may be designed for any suitable configuration task in which using such a checklist would be helpful to ensure compliance with the practice management system's configuration requirements.

A third category of configuration task is an embedded administrative task. The inventors have recognized that the efficiency of the configuration process may be improved by enabling a user at the medical practice to enter some values directly into the entries in a local tablespace for the medical practice rather than having the user convey the values to an administrator of the practice management system and then having the administrator of the practice management system enter the values into the local tablespace. Tasks that enable a user at a medical practice to directly interact with a local tablespace stored by the practice management system are described herein as embedded administrative tasks, examples of which are illustrated in FIGS. 13 and 14.

FIG. 13 illustrates an exemplary embedded administrative task in which a user at a medical practice may interact with the corresponding local tablespace for the medical practice to specify patient locations for tracking patients' physical locations during a visit to the medical practice. For example, the user may indicate entries for each exam room at the medical practices and/or any other physical locations including way stations which may serve as locations for the patient throughout the visit. By tracking the location of the patient throughout the visit, the patient workflow during the visit may be improved. A user at the medical practice may interact with the embedded administrative task to directly input values into the local tablespace.

FIG. 14 illustrates another exemplary embedded administrative task in which a user at a medical practice may interact with to specify a list of encounter reasons for patients of the medical practice. Although the list of encounter reason names may have been provided in the local tablespace as part of the pre-configuration process described earlier, a user at the medical practice may interact with the entries in the local tablespace to further specify provider and/or practice specific information regarding the encounter reasons. The user at the medical practice may also add new encounter reasons that were not added during the pre-configuration process or delete encounter reasons that were added during pre-configuration but may not be applicable to the particular medical practice.

It should be appreciated that the embedded administrative tasks illustrated in FIGS. 13 and 14 are merely examples of possible embedded administrative tasks that may be used in accordance with embodiments of the invention and other embedded administrative tasks may also be used. By empowering users at a medical practice to interface directly with data stored by the practice management system via embedded administrative tasks, the configuration time and effort for configuring a customized solution may be reduced compared to conventional practice management systems that may require an administrator of the practice management system to enter such information into the local tablespace for the medical practice.

Figure 15:
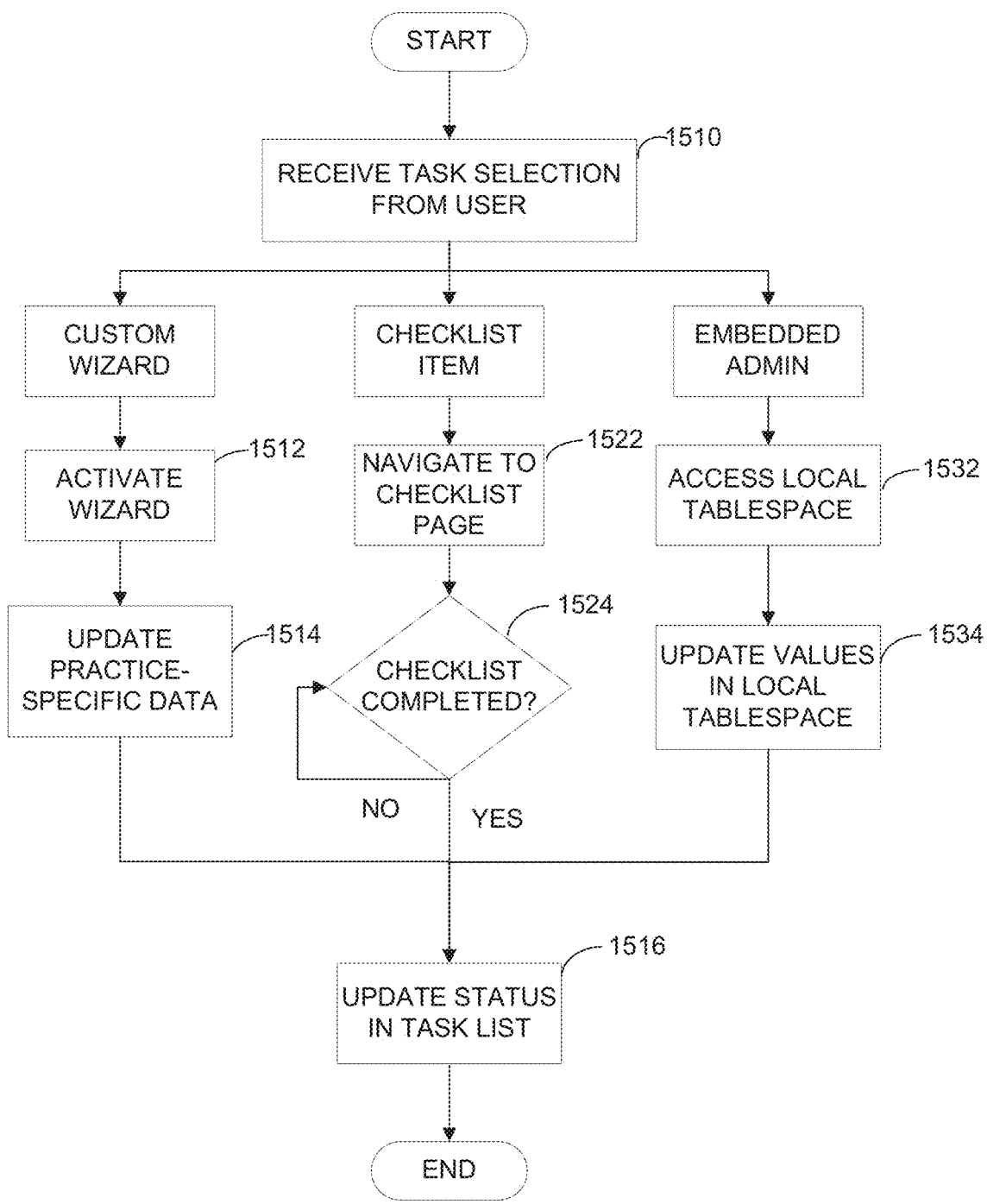
FIG. 15 is a flow chart of a task completion process for self-service implementation during a configuration process in accordance with some embodiments of the invention.

FIG. 15 illustrates a flowchart for an exemplary process for completing tasks in association with some embodiments of the invention. In act 1510, a task selection is received. For example, a user at a medical practice may select a task from the task list displayed on a dashboard screen portion of a user interface and in response to this selection, a configuration module of the practice management system may receive an indication that the user has selected a particular task.

The process then proceeds along one of a plurality of paths depending on the particular category type of the selected task. If the selected task is a custom wizard task, the process proceeds to act 1512 where the custom wizard associated with the selected task is activated. The process then proceeds to act 1514 where the local tablespace for the medical practice is updated to include the data entered by the user in the sequential screens of the custom wizard. Once the custom task has been completed, the process proceeds to act 1516 where the status for the selected task is updated to reflect that the task has been completed. In some instances, a user may perform only a partial portion of a task without completing the task. In such instances, the status of the task may be updated to reflect the partially-completed task to instruct the user at the medical practice that additional steps are necessary to complete the task.

Continuing with the description of FIG. 15, if the selected task is a checklist, the process proceeds from act 1510 to act 1522 where the configuration module of the practice management system navigates to and displays a checklist screen for the selected task for user completion. The process then proceeds to act 1524 where it is determined whether the checklist has been completed. If it is determined that the checklist has been completed, the process proceeds to act 1516 where the status associated with the selected task is updated. Although it is illustrated in FIG. 15 that the process returns to act 1524 if it is determined that the checklist is not completed, in some embodiments, a checklist may only be partially completed and the status of the checklist task may be updated accordingly in act 1516 as described above with regard to custom wizard tasks.

If the selected task is an embedded administrative task, the process proceeds from act 1510 to act 1532 where a portion of the local tablespace for the medical practice stored by the practice management system is exposed to the user of the medical practice thereby enabling direct entry of data into the local tablespace. The process then proceeds to act 1534 where in response to receiving values input by the user, the local tablespace for the medical practice is updated to reflect the changes input from the user. Once the task has been completed (entirely or partially), the process proceeds to act 1516 where the status associated with the task is updated as described above.

Figure 16:
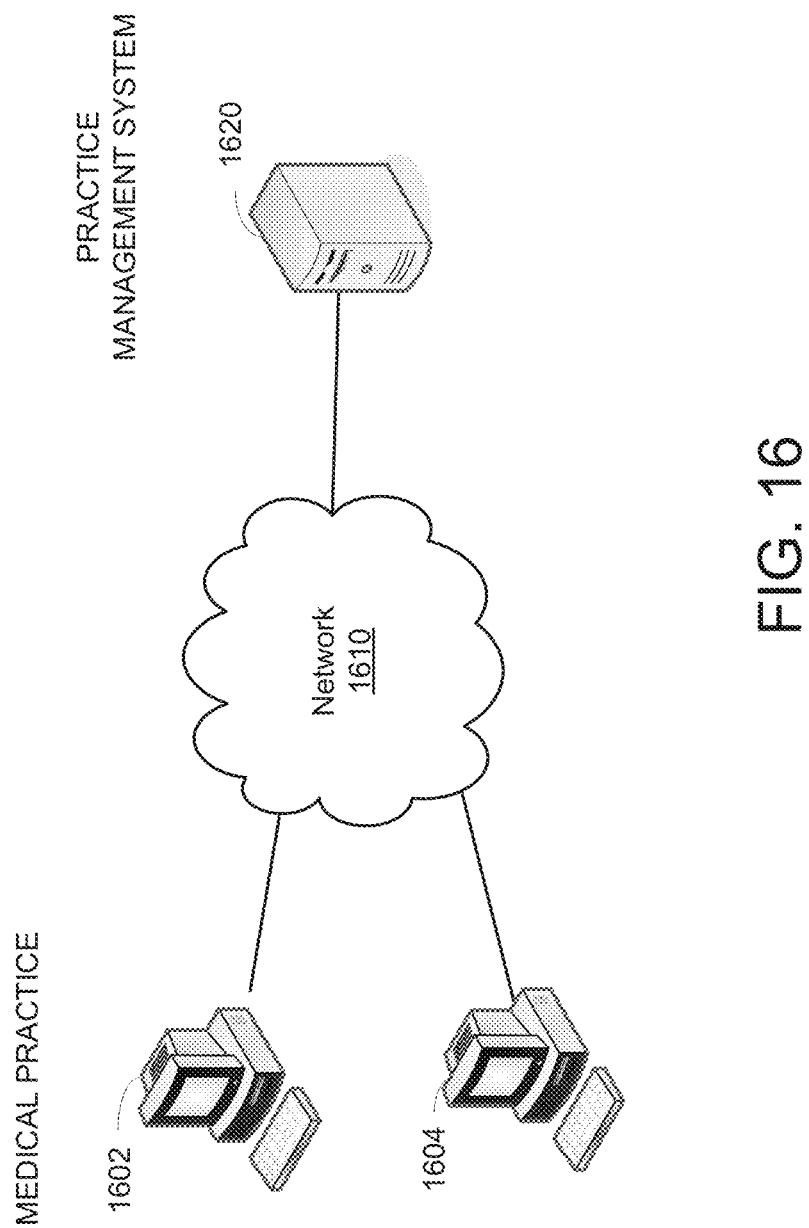
FIG. 16 is a schematic of a network environment in which some embodiments of the invention may be employed.

FIG. 16 illustrates an exemplary networked system on which some embodiments of the invention may be employed. Networked computers 1602 and 1604 located at a medical practice and computer 1620 located at a location associated with a practice management system are shown connected to a network 1610. Network 1610 may be any type of local or remote network including, for example, a local area network (LAN) or a wide area network (WAN) such as the Internet. In the example of FIG. 16, three networked computers are shown. However, it should be appreciated that network 1610 may interconnect any number of computers of various types and the networked system of FIG. 16 is provided merely for illustrative purposes. For example, computer 1620 may be connected via network 1610 (or other networks) to a plurality of computers at a plurality of medical practice locations to provide practice management services to each of the connected medical practices. As should be appreciated from the foregoing, embodiments of the invention may be employed in a networked computer system regardless of the type or network size or configuration.

Having thus described several aspects of some embodiments of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a non-transitory tangible computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein, unless clearly indicated to the contrary, should be understood to mean "at least one."

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," shall have its ordinary meaning as used in the field of patent law.

As used herein in, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of facilitating a configuration of a health information component of a practice management system including at least one processing device, the health information component being configured for use by a healthcare provider associated with a medical practice, the method comprising:
storing, by the practice management system, a plurality of global content items, wherein each of the global content items is associated with one or more specialties of a medical practice, wherein the global content items include at least one clinical health information form template including a plurality of fields for collecting health information from a patient, and at least one patient clinical workflow template;
receiving a selection of one or more specialties associated with the medical practice;
identifying based, at least in part, on the selected one or more specialties, at least one global content item of the plurality of global content items associated with the selected one or more specialties;
generating, by the at least one processor device, an initial configuration for the health information component, wherein the initial configuration is based, at least in part, on the identified at least one global content item and includes the at least one clinical health information form template and the at least one patient clinical workflow template;
receiving via a user interface, input from one or more users at the medical practice;
refining the initial configuration for the health information component based, at least in part, on the input received from the one or more users at the medical practice; and
saving the refined initial configuration as a customized configuration of the health information component for use by the healthcare provider when accessing the health information management component of the practice management system.

2. The method of claim 1, wherein receiving a selection of one or more specialties comprises receiving the selection of the one or more specialties based, at least in part, on information in a contract between the medical practice and a provider of the practice management system.

3. The method of claim 1, further comprising:
creating a task list, wherein the task list prompts the user to complete one or more tasks to facilitate refining the initial configuration; and
displaying the task list to the one or more users at the medical practice via the user interface.

4. The method of claim 3, further comprising:
tracking a completion progress of tasks on the task list; and
updating the task list when it is determined that a predetermined amount of time has elapsed and/or in response to a request to update the task list.

5. The method of claim 3, wherein the one or more tasks includes an embedded administrative task that when selected exposes a portion of a local tablespace for the medical practice to the one or more users at the medical practice for direct entry of data into the local tablespace.

6. The method of claim 3, wherein the one or more tasks includes a checklist task that when selected prompts the one or more users at the medical practice to indicate when items on the checklist have been completed.

7. The method of claim 3, wherein the one or more tasks includes a custom wizard task that when selected presents the one or more users with a plurality of sequential screens via the user interface to facilitate guided data entry.

8. The method of claim 1, wherein generating the initial configuration comprises:
creating a local tablespace for the initial configuration;
storing the local tablespace on at least one data store associated with the practice management system; and
populating the local tablespace with the identified at least one global content item.

9. The method of claim 8, further comprising:
identifying a global content entry as a duplicate entry in the local tablespace during population of the local tablespace; and preventing copying of the duplicate entry to the local tablespace in response to determining that the at least one global content entry is a duplicate entry.

10. The method of claim 9, wherein identifying a global content entry as a duplicate entry comprises:
determining a unique identifier for the global content entry;
comparing the unique identifier for the global content entry to one or more identifiers associated with entries in the local tablespace; and
identifying the global content entry as a duplicate entry when it is determined that the unique identifier matches one of the one or more identifiers associated with entries in the local tablespace.

11. The method of claim 9, further comprising:
displaying a summary screen identifying the duplicate entry as not having been copied to the local tablespace during population of the local tablespace.

12. The method of claim 8, wherein refining the initial configuration comprises modifying at least one value stored in the local tablespace.

13. The method of claim 1, wherein the health information component is configured to facilitate the management of electronic health records (EHRs).

14. At least one non-transitory computer-readable medium encoded with a plurality of instructions that, when executed by a computer, perform a method of configuring a health information component of a practice management system for use by a healthcare provider associated with a medical practice, the method comprising:
storing, by the practice management system, a plurality of global content items, wherein each of the global content items is associated with one or more specialties of a medical practice, wherein the global content items include at least one clinical health information form template including a plurality of fields for collecting health information from a patient, and at least one patient clinical workflow template;
receiving a selection of one or more specialties associated with the medical practice;
identifying based, at least in part, on the selected one or more specialties, at least one global content item of the plurality of global content items associated with the selected one or more specialties;
generating an initial configuration for the health information component, wherein the initial configuration is based, at least in part, on the identified at least one global content item and includes the at least one clinical health information form template and the at least one patient clinical workflow template;
receiving via a user interface, input from one or more users at the medical practice;
refining the initial configuration for the health information component based, at least in part, on the input received from the one or more users at the medical practice; and
saving the refined initial configuration as a customized configuration of the health information component for use by the healthcare provider when accessing the health information management component of the practice management system.

15. The at least one computer-readable medium of claim 14, wherein the method further comprises:
creating a local tablespace for the initial configuration;
storing the local tablespace on at least one data store associated with the practice management system; and
populating the local tablespace with the identified at least one global content item.

16. The at least one computer-readable medium of claim 15, wherein refining the initial configuration comprises modifying at least one value stored in the local tablespace.

17. The at least one computer-readable medium of claim 15, further comprising:
identifying a global content entry as a duplicate entry in the local tablespace during population of the local tablespace; and
preventing copying of the duplicate entry to the local tablespace in response to determining that the at least one global content entry is a duplicate entry.

18. The at least one computer-readable medium of claim 14, wherein the method further comprises:
creating a task list, wherein the task list prompts the user to complete one or more tasks to facilitate refining the initial configuration; and
displaying the task list to the one or more users at the medical practice via the user interface.

19. A computer system, comprising:
at least one server computer configured to host a practice management system including a health information management component, wherein the practice management system includes a configuration module configured to facilitate a configuration of the health information management component for a medical practice;
at least one data store associated with the practice management system, wherein the at least one data store is configured to store a plurality of global content items accessible to the configuration module to facilitate the configuration of the health information management component for the medical practice, wherein each of the global content items is associated with one or more specialties of a medical practice, wherein the global content items include at least one clinical health information form template including a plurality of fields for collecting health information from a patient, and at least one patient clinical workflow template; and
at least one client computer accessible to one or more users at the medical practice, wherein the at least one client computer is configured to display a user interface provided by the practice management system to enable the one or more users at the medical practice to participate in the configuration of the health information management component for the medical practice;
wherein the configuration module is configured to facilitate a configuration of the health information component for the medical practice by:
identifying at least one global content item of the plurality of global content items associated with one or more specialties of the medical practice;
generating an initial configuration for the health information component, wherein the initial configuration is based, at least in part, on the identified at least one global content item and includes the at least one clinical health information form template and the at least one patient clinical workflow template;
refining the initial configuration for the health information component based, at least in part, on input received via the user interface; and
saving the refined initial configuration as a customized configuration of the health information component for use by a healthcare provider of the medical practice when accessing the health information management component of the practice management system.

20. The computer system of claim 19, wherein the at least one data store is configured to store a plurality of local tablespaces representing a configuration of the health information management component for a plurality of medical practices associated with the practice management system.

21. The computer system of claim 19, wherein the at least one data store is configured to store a plurality of rules designed to manage interactions between and/or within one or more components of the practice management system.

22. The computer system of claim 19, wherein the configuration module comprises a self-service implementation tool configured to manage at least one interaction between the one or more users at the medical practice and the configuration module of the practice management system.

23. The computer system of claim 22, wherein the self-service implementation tool is configured to generate a task list including at least one task to be performed by the one or more users at the medical practice.

24. The computer system of claim 23, wherein the self-service implementation tool is configured to track a status of the at least one task on the task list.

* * * * *